US012661026B2

(12) United States Patent
Weekamp et al.

(10) Patent No.: US 12,661,026 B2
(45) Date of Patent: Jun. 23, 2026

(54) SENSOR COMPRISING AN INTERCONNECT AND AN INTERVENTIONAL MEDICAL DEVICE USING THE SAME

(71) Applicant: KONINKLIJKE PHILIPS N.V., Eindhoven (NL)

(72) Inventors: Johannes Wilhelmus Weekamp, Beek en Donk (NL); Vincent Andrianus Henneken, Utrecht (NL); Marcel Mulder, Eindhoven (NL); Marcus Cornelis Louwerse, Nijmegen (NL); Arjen Van der Horst, Tilburg (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 898 days.

(21) Appl. No.: 17/922,642

(22) PCT Filed: Apr. 21, 2021

(86) PCT No.: PCT/EP2021/060287
§ 371 (c)(1),
(2) Date: Nov. 1, 2022

(87) PCT Pub. No.: WO2021/224000
PCT Pub. Date: Nov. 11, 2021

(65) Prior Publication Data
US 2023/0165477 A1     Jun. 1, 2023

(30) Foreign Application Priority Data
May 8, 2020     (EP) ..................................... 20173625

(51) Int. Cl.
*A61B 5/026*     (2006.01)
*A61B 5/00*     (2006.01)
*A61B 8/00*     (2006.01)

(52) U.S. Cl.
CPC ............ *A61B 5/026* (2013.01); *A61B 5/6852* (2013.01); *A61B 8/4444* (2013.01); *A61B 2562/02* (2013.01)

(58) Field of Classification Search
CPC ... A61B 5/026; A61B 5/6852; A61B 2562/02; A61B 2562/0204; A61B 2562/12;
(Continued)

(56) References Cited

U.S. PATENT DOCUMENTS

2011/0218437 A1     9/2011   Park
2016/0271651 A1*    9/2016   Petersen ................... B06B 1/06
(Continued)

FOREIGN PATENT DOCUMENTS

EP          0145429 A2      6/1985
EP          0739656 A2     10/1996
(Continued)

OTHER PUBLICATIONS

International Search Report and Written Opinion of PCT/EP2021/060287, dated Jul. 19, 2021.

*Primary Examiner* — Emily P Pham

(57) ABSTRACT

A sensor has a sensor element (5) with two opposite sides (11, 9) and an interconnect (7) with first and second terminal segments (13B, 13F) interconnected by an intermediate segment (42). The first terminal segment (13F) is positioned against a first side (11) of the sensor element and comprises a first contact terminal (50). The second terminal segment (13B) is positioned against the second side (9) of the two opposite sides of the sensor element and comprises a second contact terminal (52) on a surface facing the second side (11). There are third and fourth, external, contact terminals (54, 56). The interconnect provided electrical connections between the first and fourth contact terminals (50, 56) and between the second and third contact terminals (52, 54).

15 Claims, 15 Drawing Sheets

(58) Field of Classification Search

CPC ..... A61B 8/4444; A61B 8/445; A61B 8/4455; A61B 8/4483; A61B 8/4494; B06B 1/0655; B06B 2201/76; G10K 9/122; G10K 9/22; G01H 11/08; G01S 15/8922; G01S 15/8979; H10N 30/06; H10N 30/302; H10N 30/875

See application file for complete search history.

(56) References Cited

U.S. PATENT DOCUMENTS

| | | |
|---|---|---|
| 2021/0007711 A1* | 1/2021 | Van Der Horst ........ A61B 8/06 |
| 2021/0106280 A1 | 4/2021 | Weekamp |
| 2022/0131065 A1 | 4/2022 | Weekamp |

FOREIGN PATENT DOCUMENTS

| | | | |
|---|---|---|---|
| EP | 2165650 | A1 | 3/2010 |
| JP | S61103399 | A | 5/1986 |
| JP | 2007047023 | A | 2/2007 |
| WO | 2015093358 | A1 | 6/2015 |
| WO | 2015137251 | A1 | 9/2015 |

* cited by examiner

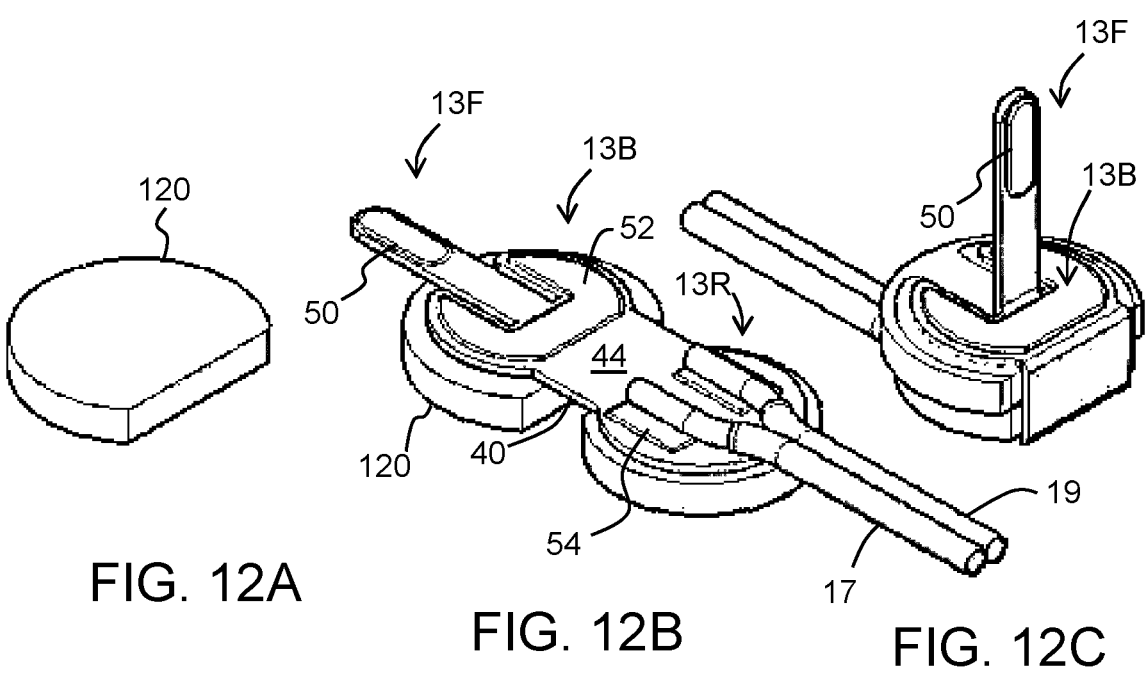
FIG. 12A
FIG. 12B
FIG. 12C
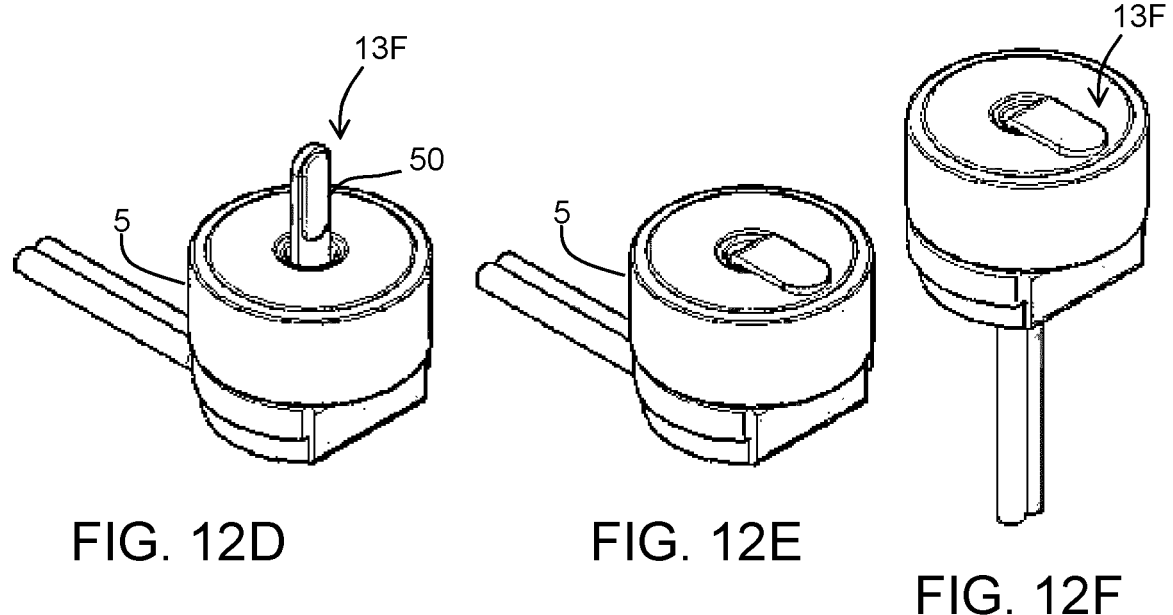
FIG. 12D
FIG. 12E
FIG. 12F

SENSOR COMPRISING AN INTERCONNECT AND AN INTERVENTIONAL MEDICAL DEVICE USING THE SAME

CROSS-REFERENCE TO PRIOR APPLICATIONS

This application is the U.S. National Phase application under 35 U.S.C. § 371 of International Application No. PCT/EP2021/060287, filed on Apr. 21, 2021, which claims the benefit of European Patent Application No. 20173625.3, filed on May 8, 2020 These applications are hereby incorporated by reference herein.

FIELD OF THE INVENTION

The present invention relates to a sensor, a medical device comprising the sensor and a method for manufacturing the sensor.

BACKGROUND OF THE INVENTION

Measuring blood flow in arteries helps physicians in making the right diagnoses for proper treatment. The measuring principle can be based on spectral Doppler. The actuator/receiver for such a device can be based on a circular disk of piezo electric material with electrodes on the front and back sides. The electrical interconnection to the actuator/receiver is made by soldering wires on both the front and back surfaces of the piezo disk. This is the current state of the art for intravascular flow sensing. Another application using piezo electric material is for localization of sensors on devices in an ultrasound field, where again circular disk transducers can be used.

Piezo disks having electrical connections made by soldering wires often have reduced or limited sensitivity and distortion due to the presence of wires and soldering material. The amount of soldering material, which is applied for the electrical connection can limit the transducer resonance performance, at the cost of acoustic pressure output.

A state of the art piezo disk 2 is shown in FIGS. 1A to 1C. In FIG. 1A, the back side 4 of the disk 2 is shown. In FIG. 1B the front side 6 of the same piezo disk 2 is shown. The electrical connections to the front and backsides are made by soldering copper wires: a front wire 8 and a back wire 10 attached to the front side 6 and the back side 4 of the disk 2, respectively. The piezo disk 2 has a hole for the front wire 8 to run through. The quantity of soldering material 3 needed to fix the front wire 8 might cover a substantial part of the front side 6. There can then be a loss of acoustical pressure due to the reduced active surface 6 of the piezo disk. An exemplary top view of the front side 6 is shown in FIG. 1C, where the solder covers about a quarter of the front side 6.

The ceramic disc also has a very small size, such as a diameter of around 300 μm. The wires are therefore extremely small, with typical wire diameters in the range of 20-40 μm. Due to the extremely small dimensions of both the transducer and the electrical wires, a reliable and reproducible connection is also very difficult to achieve using this soldering method, leading to relatively high yield loss. In particular, the amount of solder 3 that is applied on a transducer front surface 6 is difficult to control and can influence the transducer resonance performance and acoustic pressure output.

The applicant has proposed, but not yet published, in European patent application no. 19155417.9, a sensor having a sensor element, an interconnect and a metallic layer.

The interconnect is configured to be arranged at the sensor element and it extends from one side of the sensor element to the other side of the sensor element, around an outer peripheral edge. The electrical connections to the sensor element can then be made at the same side of the sensor element.

The interconnect comprises a thin single sided metalized film that is bonded and wrapped around the sensor element. It avoids the need for soldering and also passing the thin wires through an opening in the sensor element.

The design has to take account of the conductive outer surface of the interconnect. Thus, there are some design constraints. There remains a need to provide further transducer designs with improved performance and integration of sensors in medical devices having dimensional constraints.

SUMMARY OF THE INVENTION

The invention is defined by the claims.

According to the present invention, there is provided a sensor, comprising:

a sensor element with first and second opposite sides; and an interconnect comprising an electrically insulating flexible carrier, wherein the interconnect comprises first and second terminal segments interconnected by an intermediate segment, wherein the first terminal segment is positioned against the first side of the sensor element and comprises a first contact terminal on a surface facing the first side, wherein the second terminal segment is positioned against the second side of the sensor element and comprises a second contact terminal on a surface facing the second side, wherein the interconnect further comprises third and fourth, external, contact terminals, and wherein the interconnect further comprises a first internal electrical connection within the flexible carrier which connects the first contact terminal and the fourth contact terminal and a second internal electrical connection within the flexible carrier which connects the second and third contact terminals.

This sensor has an interconnect which provides an internal connection which extends between opposite sides of the sensor element, from one sensor terminal at one side of the sensor element to a first external terminal. Because it is shielding within the insulating carrier, this means it can pass along any desired path, such as through an opening or around the outside of the sensor element. Another internal connection extends from the other side of the sensor element to a second external terminal. The interconnect thus provides two external contact terminals for the sensor as well as making contact to opposite sides of the sensor element. Direct wire connections to the sensor element are avoided. Instead connections to the sensor element are by means of the first and second contact terminals. These connections may be made by physical pressure or by contact pad soldering (rather than wire soldering), by gluing, or any other suitable connection method.

In a first set of examples, the third and fourth contact terminals are on the second terminal segment, on the opposite side of the carrier to the second contact terminal. In this design, only the first and second terminal segments are required. The second terminal segment is double sided; one side faces the sensor element and the other side faces outwardly, forming the external contact face for the sensor. The second, internal, electrical connection between the second and third contact terminals may for example be a via extending through the carrier.

In a second set of examples, the third and fourth contact terminals are on a third terminal segment of the interconnect, the third terminal segment being interconnected to the second terminal segment by a second intermediate segment.

In this set of examples, there are three terminal segments in a line, with two intermediate segments. In this case, the interconnect may have a folded configuration with a space between the sensor element and the third terminal segment. This space may for example be used for acoustic damping.

The third and fourth contact terminals may then be on the same side of the carrier as the second contact terminal. The second contact terminal faces the second side of the sensor element, and the third and fourth contact terminals face outwardly. They may face in the opposite direction after a 180 degree bend in the second intermediate segment.

Alternatively, there may be a 90 degree bend or a Z-bend in the second intermediate segment so that the third and fourth contact terminals lie in a plane perpendicular to the second side of the sensor element. This may allow wire connections to be made with no bends. The (first) intermediate segment folds through or around the sensor element to extend between the opposite sides.

The second terminal segment may be connected to a first base unit. The first base unit may be a de-matching or attenuating backing layer for the sensor element.

Instead or as well, the third terminal segment may be connected to a second base unit. This for example provides additional rigidity and assists in handling and processing.

The first or second base unit for comprises active electronic components such as components of an ASIC.

The second intermediate segment for example extends around an outer edge of the first and/or second base unit.

In an example with both first and second base units, the second intermediate segment may extend around an outer edge of the first base unit and the second base unit may extend at 90 degrees to the first base unit. This provides the external third and fourth contact terminals in a plane which is parallel to the direction in which the external connection wires typically extend, thereby avoiding the need for bends at the ends of the wires where they connect to the third and fourth contact terminals.

The sensor for example further comprises a first wire connected to the third contact terminal and a second wire connected to the fourth contact terminal. These wires provide the sensor connections to external circuitry. The first and second wires then each have ends which are connected to the third and fourth contact terminals.

These connections may be parallel to a plane in which the third and fourth contact terminals extend. Thus, the ends of the wires are connected flat against the contact terminals. Instead, the connections may be perpendicular to the plane in which the third and fourth contact terminals extend. Thus, the connections may be made with the wires connected at their tips to the contact terminals, for example connected by a solder bump.

In all examples above, the (first) intermediate segment of the carrier may be located adjacent to a lateral outer side of the sensor element and the first and second terminal segments are folded over the first and second sides of the sensor element. This is for example suitable for a sensor having a block shape. The intermediate segment extends around an outer edge.

Instead, the sensor element may comprise a central opening, the intermediate segment is folded relative to the second terminal segment, the intermediate segment of the carrier passes through the central opening, and the first terminal segment is folded over the first side of the sensor element. The intermediate segment for example has no external conducting portions, so it can safely be positioned through a central opening of the sensor element.

The sensor element is for example an ultrasound sensor element.

The first side of the ultrasound sensor is for example configured for acoustical matching for emission and reception of ultrasound waves to and from anatomical media.

The second side of the ultrasound transducer may for example be provided with electrically conductive ultrasound attenuating material.

The invention also provides an interventional medical device, comprising:

a sensor as defined above; and an elongate body, wherein the sensor is mounted at a distal end of the elongate body.

The elongate body may be a catheter or a guidewire, for in-vessel body sensing, for example for ultrasound flow sensing.

The invention also provides a method of manufacturing a sensor, comprising:

providing a sensor element with two opposite sides;

providing an interconnect comprising an electrically insulating flexible carrier, wherein the carrier comprises first and second terminal segments interconnected by an intermediate segment;

bending the interconnect such that:

the first terminal segment is against the first side of the two opposite sides of the sensor element with a first contact terminal facing the first side; and the second terminal segment is against the second side of the two opposite sides of the sensor element with a second contact terminal facing the second side; and using the interconnect to provide a first internal electrical connection within the flexible carrier which connects the first contact terminal to a fourth, external, contact terminal and to provide a second internal electrical connection within the flexible carrier which connects the second contact terminal to a third, external, contact terminal.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings, in which:

FIGS. 12A to 12F show a ninth example of a sensor in accordance with the invention;

DETAILED DESCRIPTION OF EMBODIMENTS

Figures 1A, 1B, 1C:
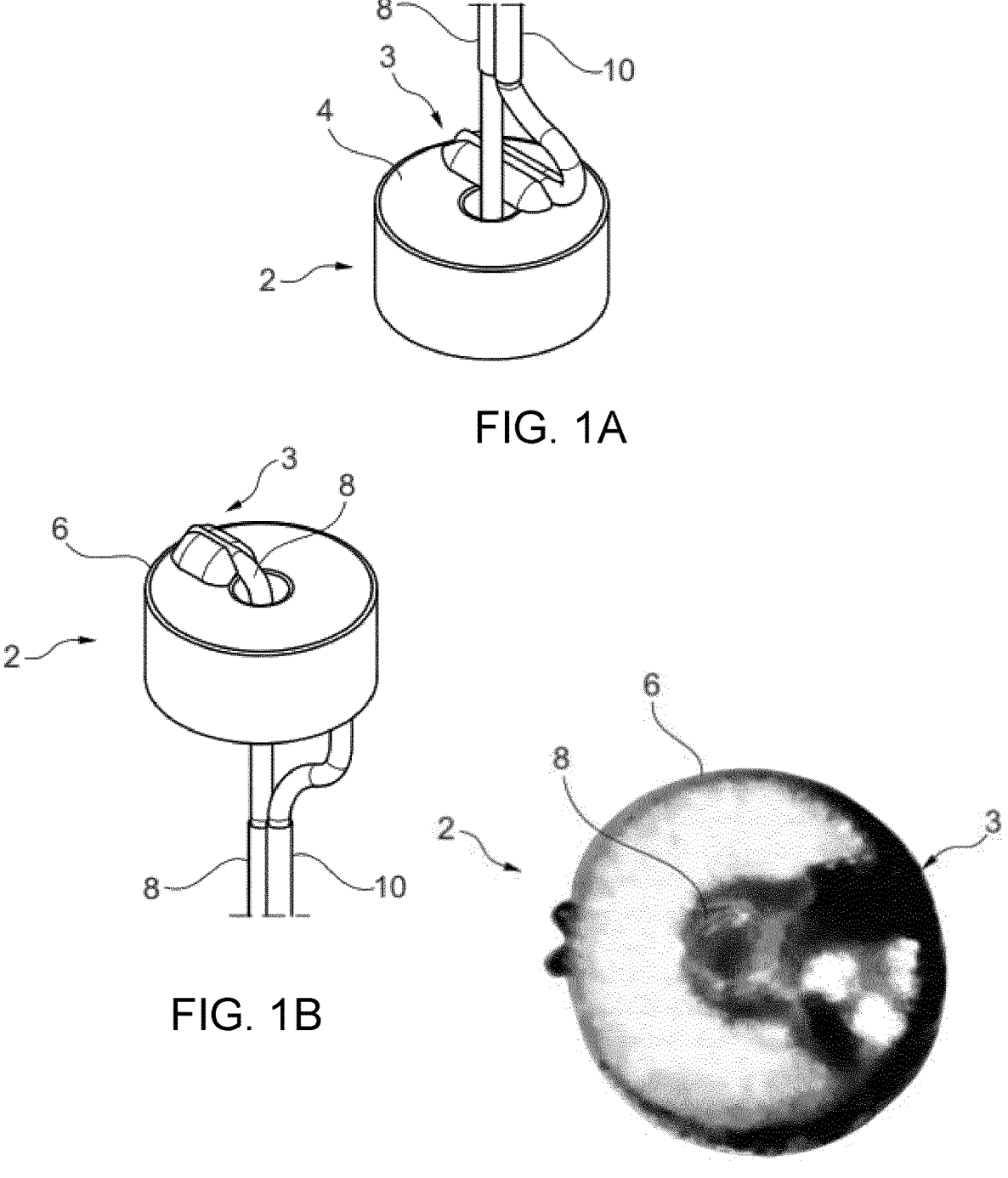
FIGS. 1A to 1C show a known piezo sensor and its connection to external wires.

Certain embodiments will now be described in greater details with reference to the accompanying drawings. In the following description, like drawing reference numerals are used for like elements, even in different drawings. The matters defined in the description, such as detailed construction and elements, are provided to assist in a comprehensive understanding of the exemplary embodiments. Also, well-known functions or constructions are not described in detail since they would obscure the embodiments with unnecessary detail. Moreover, expressions such as "at least one of", when preceding a list of elements, modify the entire list of elements and do not modify the individual elements of the list.

The invention provides a sensor having a sensor element with two opposite sides and an interconnect with first and second terminal segments interconnected by an intermediate segment. The first terminal segment is positioned against a first side of the sensor element and comprises a first contact terminal. The second terminal segment is positioned against the second side of the sensor element and comprises a second contact terminal on a surface facing the second side. There are third and fourth, external, contact terminals. The interconnect provides electrical connections between the first and fourth contact terminals and between the second and third contact terminals.

The invention is modification to a previously proposed (but not yet published) sensor design of the applicant.

Figures 2A, 2B, 3A, 3B:
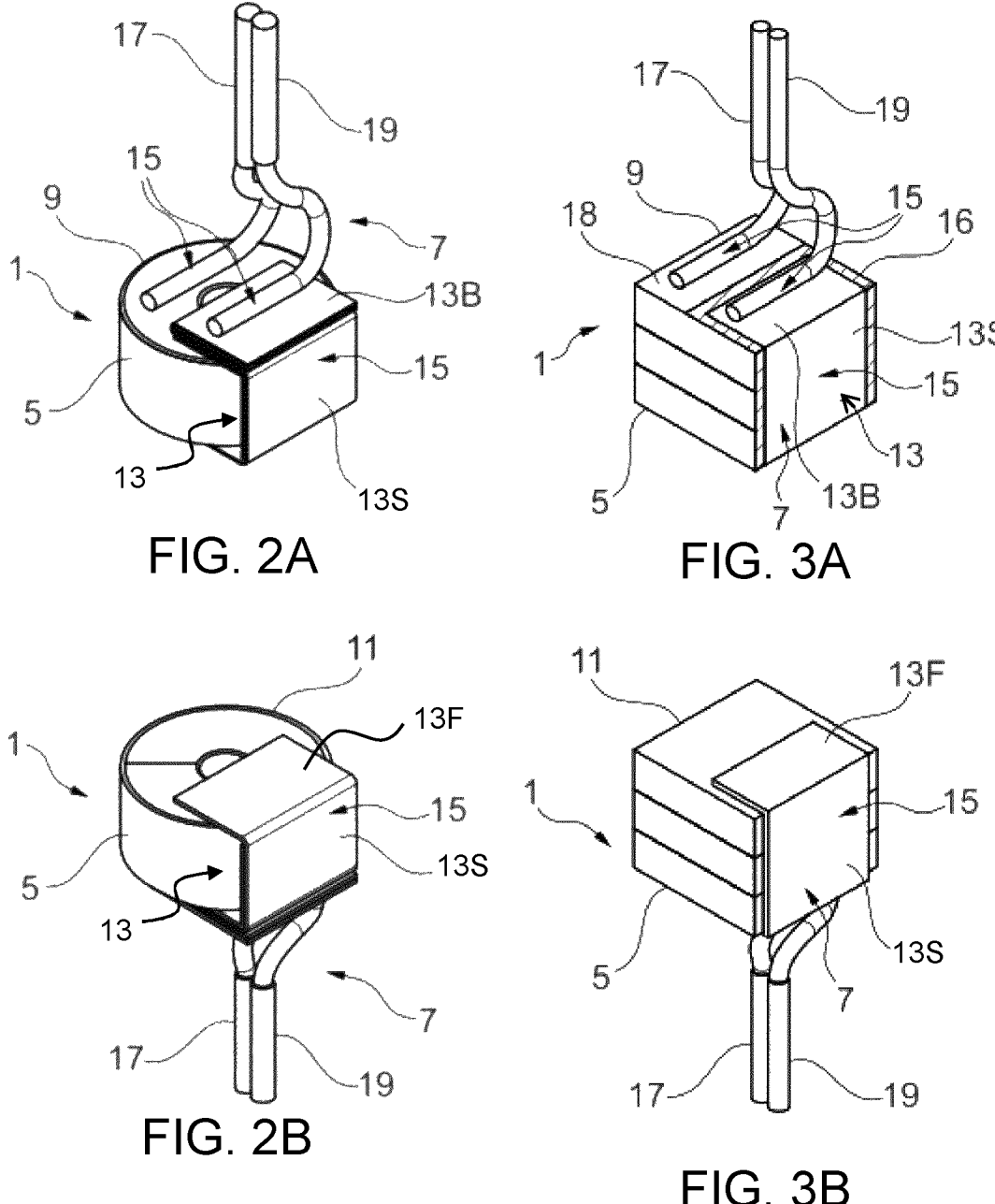
FIGS. 2A and 2B show an example of a sensor as proposed in European patent application no. 19155417.9.
FIGS. 3A and 3B show another example of a sensor as proposed in European patent application no. 19155417.9.

FIGS. 2A and 2B show an example of a sensor 1 as proposed in European patent application no. 19155417.9.

The sensor 1 comprises a sensor element 5. FIG. 2A shows a back side 9 of the sensor element 5. The back is the side to which external wire connections are made and the front is the side at which sensing takes place. FIG. 2B shows a front side 11 of the sensor element 5. The sensor 1 comprises an interconnect 7. The interconnect 7 is arranged at the sensor element 5 and comprises a carrier film 13, a back wire 17 and a front wire 19 each provided with a metallic layer 15. The carrier film 13 comprises a front part 13F, a side part 13S and a back part 13B.

The front and back wires 17, 19 are provided with a bend, so that the ends of the wires 17, 19 are substantially parallel to and above the back side 9 of the sensor element 5. The interconnect 7 provides an electrical connection for the sensor element 5.

The carrier film 13 (or its front part 13F and back part 13B) is bonded on the front side 11 and at the back side 9, respectively, with a non conducting thin double sided adhesive (not visible in the figures).

The metallic layer 15 is provided on the side of the carrier film 13 facing the sensor element 5. An insulating layer is provided between the side part 13S and the sensor element 5, and between the back part 13B and the sensor element 5. The front part 13F of the carrier film 13 is arranged at the front side 11 of the sensor element 5.

The carrier film 13 is wrapped around the side to the back side 9 of the sensor element 5. The interconnect 7 attached at the front side 11 of the sensor element 5 is thus brought to the back side 9 of the sensor element 5.

The front wire 19 is provided with a metallic layer 15 comprising Au, Pt, Ag or other noble metals, at least in the region where the wire 19 is contacting the carrier film 13. The electrical connection is provided by the front wire 19 attached to the back part 13B of the carrier film 13 and by the back wire 17 directly bonded to the back side 9 providing a metal plated surface 18 of the sensor element 5. The metal plated surface of the back side 9 can comprise Au, Pt or other noble metals as for the metallic layer 15. The electrical connection is provided at the back side 9 of the sensor element 5. The metalized carrier film 13 is for example provided as thin film.

FIGS. 2A and 2B show a sensor element with a central opening. European patent application no. 19155417.9 also discloses other possible sensor designs.

FIGS. 3A and 3B show an equivalent design for a block-shaped transducer. The same interposers are given the same reference numerals. FIG. 3A also shows the insulator 16 which is provided between the side part 13S and the sensor element 5, and between the back part 13B and the sensor element 5.

This approach needs a particular bending method because the metallization is only present on a single side of the thin film. In addition, as the metallization is on the outside of the film, connecting through the central hole of the sensor element is not feasible as making contact to the piezo material inside the central hole is difficult to avoid. Thus, even with disc shaped sensor elements, the approach above uses an interconnect which is folded around the outside of the sensor element.

The invention provides a design in which the interconnect has internal connections. There are two internal connections; one between one side of the sensor element and a first external terminal and another between the other side of the sensor element and a second external terminal. The external connections are only made to the interconnect (to the first and second external terminals) so that the connection design can be optimized. Thus, no external wire connections are needed to the sensor element itself. As will be clear from the examples below, these features enable various new sensor designs.

FIG. 4 shows a first example in accordance with the invention.

Figures 4A, 4B, 4C, 4D, 4E, 4F, 4G, 4H, 4I, 4J:
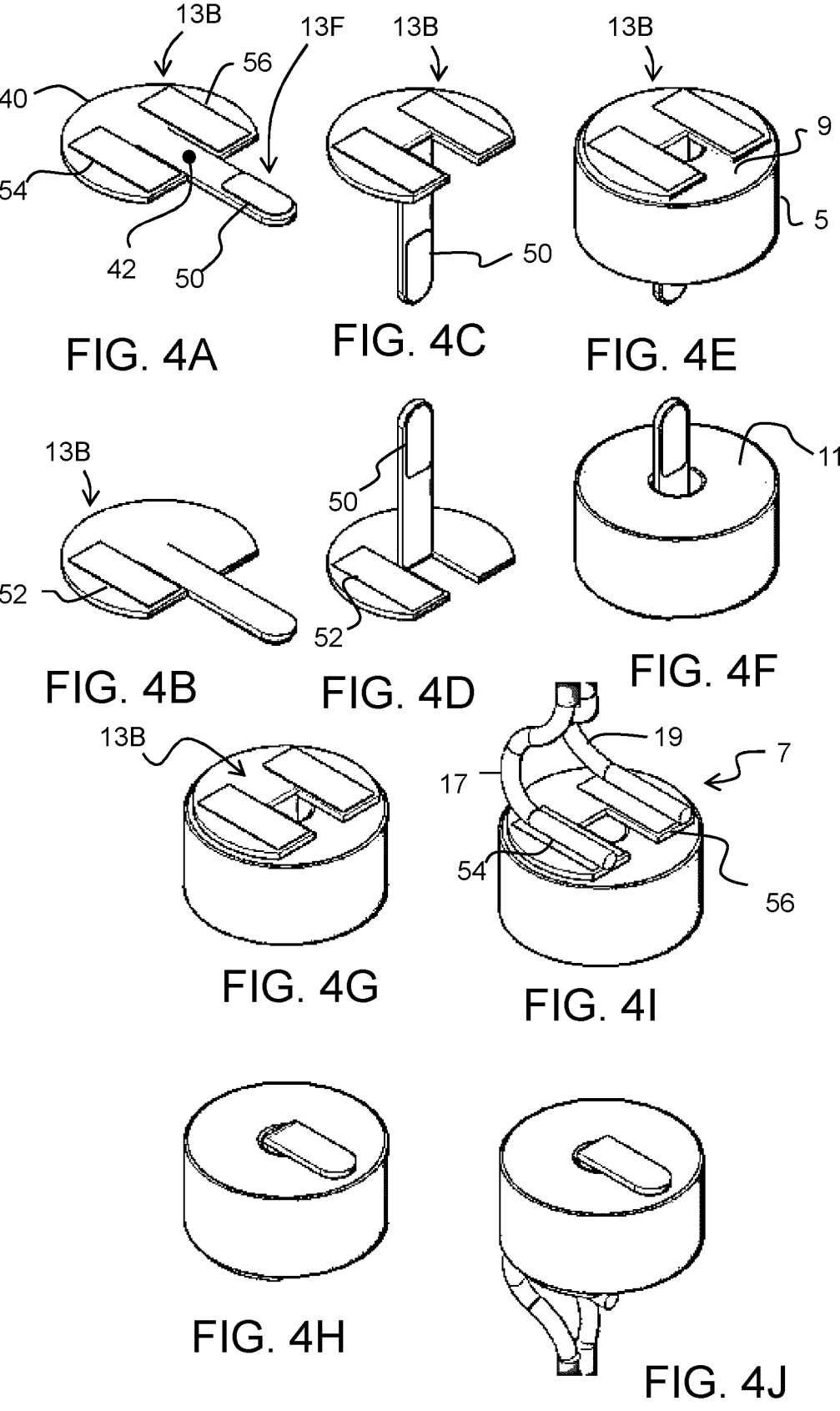
FIGS. 4A to 4J show a first example of a sensor in accordance with the invention.

FIGS. 4A and 4B show an electrically insulating flexible carrier 40 which by itself will be termed an interposer, and is to form part of an interconnect between a sensor element and external wires. The interconnect comprises the interposers between the sensor element and external circuitry, i.e. the interposer and the connections to external wires. FIG. 4A shows one side from a top view and FIG. 4B shows an opposite side from a bottom view. As in the examples above, the flexible carrier 40 comprises first and second terminal segments 13F and 13B interconnected by an intermediate segment 42.

The first terminal segment 13F is for positioning against a first side (front) of the sensor element and comprises a first contact terminal 50 on a surface which will face the first side of the sensor element.

The second terminal segment 13B is for positioning against a second side (back) of the sensor element and comprises a second contact terminal 52 on a surface which will face the second side.

The intermediate segment is for passing around or through the sensor element between the two sides.

The flexible carrier 40 further comprises third and fourth, external, contact terminals 54, 56.

A first internal electrical connection is within the flexible carrier 40 and connects first contact terminal 50 and the fourth contact terminal 56 and a second internal electrical connection within the flexible carrier connects the second and third contact terminals 52,54. Thus, the internal connections couple one external terminal to one side of the sensor element, and couple the other external terminal to the other side of the sensor element.

FIGS. 4A and 4B show the interposer in a flat state in which it is manufactured.

FIGS. 4C (top view) and 4D (bottom view) show the interposer after the intermediate segment is bent to 90 degrees relative to the plane of the second terminal segment, so that the first contact terminal can be pushed through a central opening of a sensor element.

FIGS. 4E (top view) and 4F (bottom view) show the interposer after the first contact terminal has been pushed through the central opening of a sensor element 5.

The second terminal segment 13B is against the second side 9 (back) of the sensor element 5 and the second contact terminal 52 makes electrical contact with a terminal on that side of the sensor element 5.

The first terminal segment 13F now projects through the central opening.

FIGS. 4G (top view) and 4H (bottom view) show the interposer after the first contact terminal has been bent around so that the first contact terminal 50 is positioned against the first side 11 (front) of the sensor element and the first contact terminal 50 makes electrical contact with a terminal on the front side of the sensor element 5.

FIGS. 4I (top view) and 4J (bottom view) show the connection of external wires 17, 19 to the third and fourth (external) contact terminals 54,56.

The flexible carrier and wire connections define an interconnect 7. One of the internal connections extends between opposite sides of the sensor element (through the central hole in this example), from one sensor terminal at one side of the sensor element to a first external terminal. This means it can pass along any desired path, such as through an opening as shown. Another internal connection extends from the other side of the sensor element to a second external terminal. Wire connections directly to the sensor element are avoided. Instead, connections to the sensor element itself are by means of the first and second contact terminals. These connections may be made by physical pressure or by soldering, by gluing, or by any other suitable connection method.

The interposer as presented in FIG. 4 requires electrical connection pads both on the front side as well as on the backside. Electrical vias inside the interposer may be used for connecting the front side and backside electrical connection terminals (i.e. pads).

The interposer may for example be realized using a conventional double-sided flex PCB technology with front-to-backside metallization (vias). Suitable flexible substrate materials can for example be polyimide or LCP (liquid crystal polymer).

Alternatively, the interposer could be realized using the so-called Flex-to-Rigid (F2R) technology. The F2R technology is an interconnect manufacturing platform that has been developed to integrate complex electronic sensing and imaging functionality on the tip of catheters and guidewires. It is based on the same microfabrication technologies that are used for the fabrication of cMUT transducers. It allows for the fabrication of arbitrary shaped silicon islands, of arbitrary size and thickness that contain (cMUT) ultrasound transducers, sensors, ASICs and/or passive interposers.

F2R allows flexible interconnects, consisting of a metal routing layer sandwiched between two layers of flexible polyimide, to be fabricated on a silicon wafer. This is followed by a separation step whereby individual elements are singulated by Deep Reactive Ion Etching (DRIE) and Reactive Ion Etching (ME). The F2R fabrication is based on standard IC fabrication technology, which allows the devices to scale down so that all kind of sensing functionalities and electronics can be integrated into the tip of a catheter.

The metal routing layer of the F2R technology may thus be used to form the internal electrical interconnections between contact terminals of the interposer, while maintaining an electrically insulating outer surface (other than the contact terminals themselves).

A suitable method to realize the electrical connections between the interposer contact terminals and the transducer is by applying pressure to achieve gold-gold contact. A suitable metal surface finish on the interposer contact terminals may for example be obtained through the well-known ENIG (electroless nickel immersion gold) or ENEPIG (electroless nickel electroless palladium immersion gold) plating steps. Firstly, an appropriate amount of suitable adhesive is applied between the electrode pads that need to be bonded. Secondly, sufficient pressure is applied to squeeze out any excess of adhesive until the gold on the opposing electrode pads touch each other, and thereby form an electrical connection.

By applying the second step on the front side and the backside simultaneously, both transducer connections may be achieved in a single action.

Another method to realize the electrical connections between the interposer and the transducer is by pre-applying solder on the electrical contact terminals, and reflowing the solder after the flex has been folded around the transducer.

FIG. 5 shows a modification to FIG. 4 in which electrical connections are made between the interposer and the transducer by pre-applying solder on the electrical pads and reflowing the solder after the interposer is folded around the transducer.

Figures 5A, 5B, 5C, 5D, 5E, 5F, 5G, 5H, 5I, 5J, 5K, 5L:
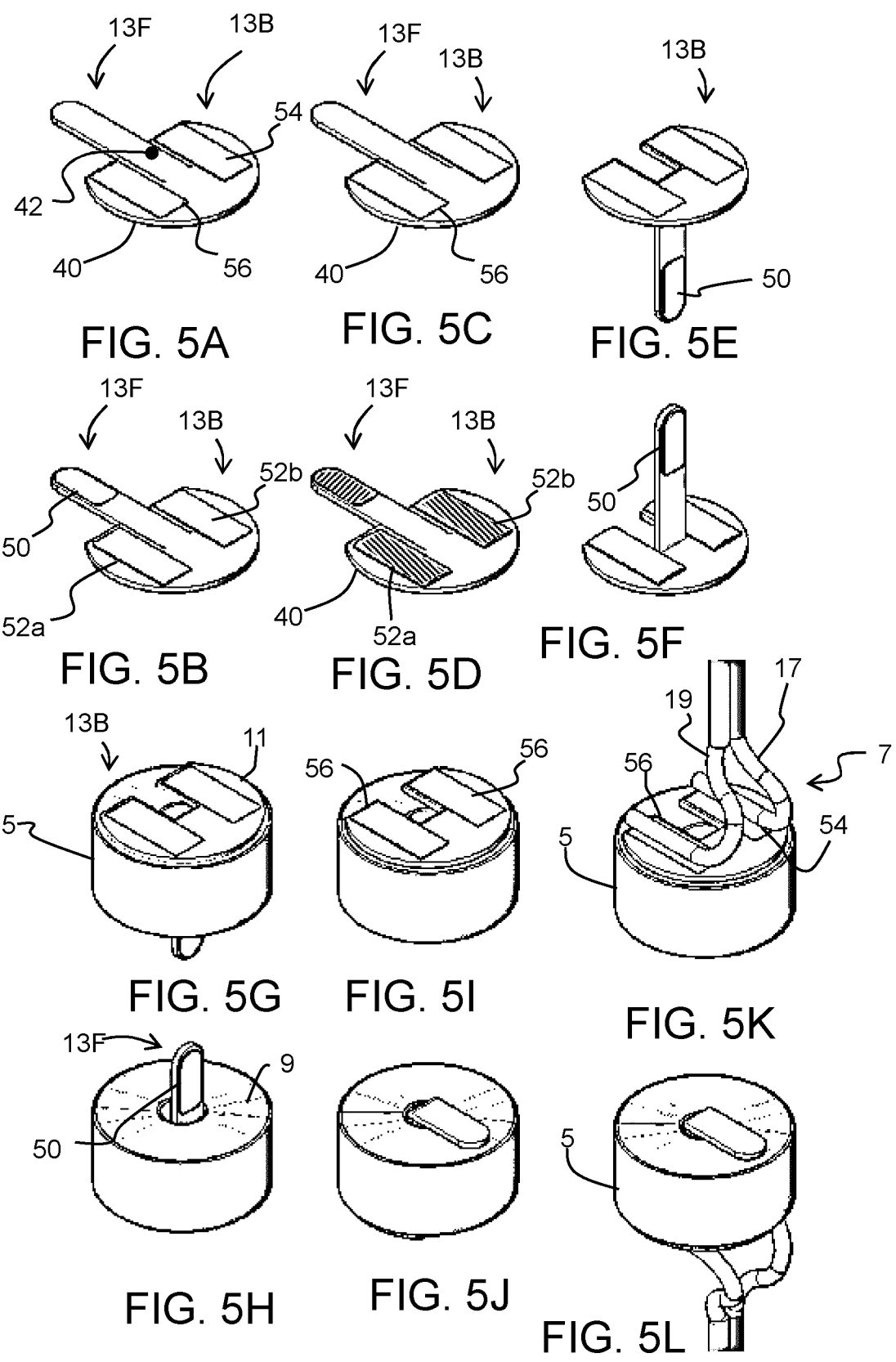
FIGS. 5A to 5L show a second example of a sensor in accordance with the invention.

FIGS. 5A and 5B show the interposer in a flat state in which it is manufactured. In order to enable the solder to be applied to one plane, the first and second electrodes 50, 52 are on the same side of the interposer (unlike the arrangement of FIG. 4). The second electrode 52 is also split into two sections 52a, 52b.

FIGS. 5C (top view) and 5D (bottom view) show the interposer after the solder has been applied to the first and second electrode terminals, shown by hatching in FIG. 5D.

FIGS. 5E (top view) and 5F (bottom view) show the interposer after the intermediate segment 42 is bent to 90 degrees, so that the first contact terminal 50 can be pushed through a central opening of a sensor element.

FIGS. 5G (top view) and 5H (bottom view) show the interposer after the first contact terminal 50 has been pushed through the central opening of a sensor element 5.

The second terminal segment 13B is against the second side 9 (back) of the sensor element 5 and the second contact terminal 52 makes electrical contact with a terminal of the sensor element 5.

The first terminal segment 13F now projects through the central opening.

FIGS. 5I (top view) and 5J (bottom view) show the interposer after the first contact terminal has been bent around so that the first contact terminal 50 is positioned against the first side 11 (front) of the sensor element and the first contact terminal 50 makes electrical contact with a terminal of the sensor element 5.

FIGS. 5K (top view) and 5L (bottom view) show the connection of external wires 17, 19 to the third and fourth (external) contact terminals 54,56.

A suitable wire connection to the interposer can be achieved by connecting exposed wire ends to the electrode pads at the proximal side of the resulting transducer subassembly. The wire connections can be realized by any suitable means known in the field, for example by soldering or ultrasonic bonding.

The sensor element may have other shapes, e.g. a square or rectangular block.

FIG. 6 shows an example with a block-shaped transducer.

As in the examples above, the interposer has first and second terminal segments 13F, 13B interconnected by an intermediate segment 42. The first terminal segment 13F has the first contact terminal 50 on a surface which will face the first side of the sensor element. The second terminal segment has a second contact terminal 52 on a surface which will face the second side. In this example, the contact terminals 50 and 52 are on the same side of the interposer, which wraps around a lateral edge of the sensor element. The interposer further comprises third and fourth, external, contact terminals 54, 56.

Figures 6A, 6B, 6C, 6D, 6E, 6F:
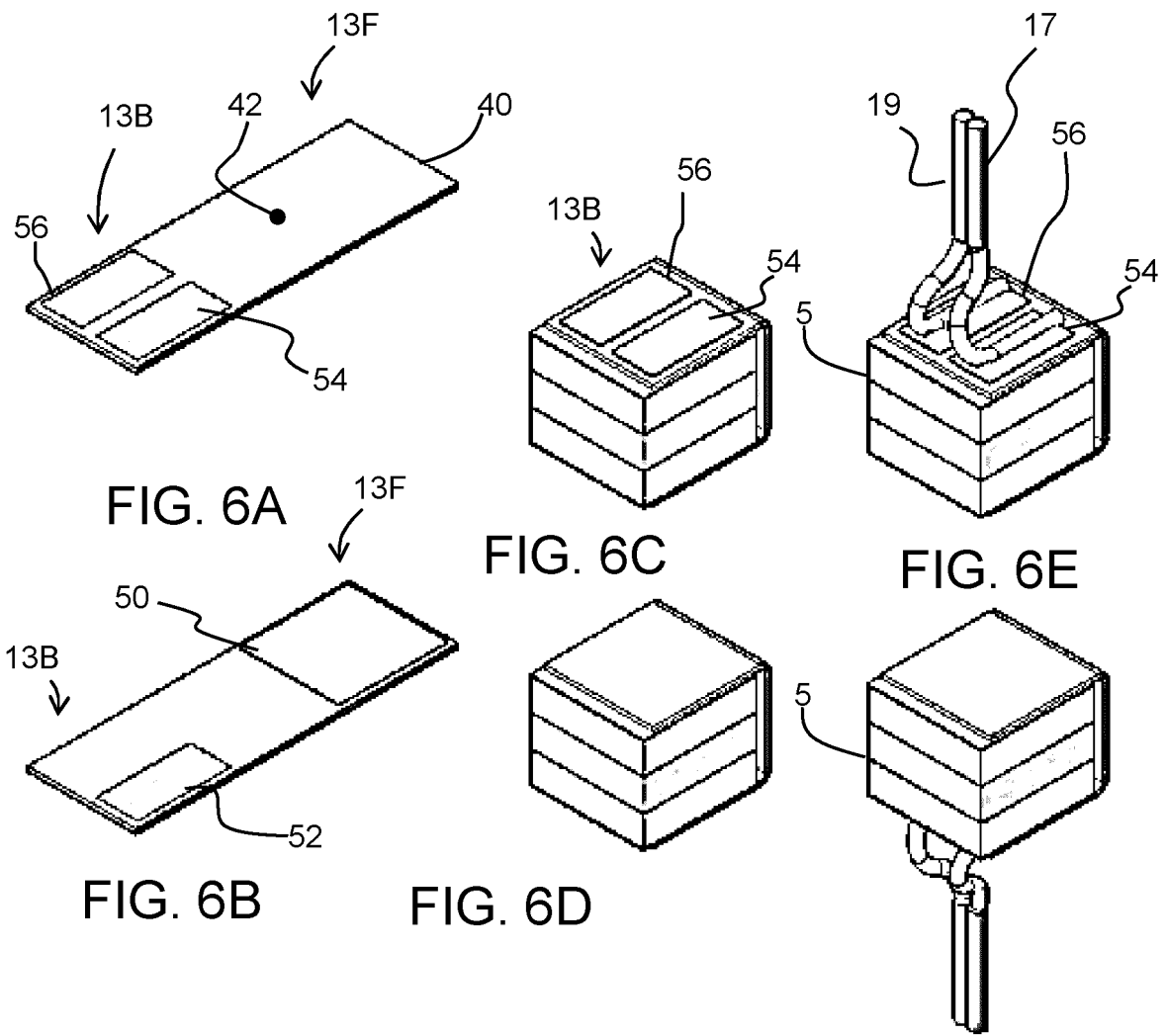
FIGS. 6A to 6F show a third example of a sensor in accordance with the invention.

FIGS. 6A (top view) and 6B (bottom view) show the interposer in a flat state in which it is manufactured.

FIGS. 6C (top view) and 6D (bottom view) show the interposer after wrapping around the sensor element 5.

FIGS. 6E (top view) and 6F (bottom view) show the connection of external wires 17,19.

As mentioned above, the F2R process allows formation of silicon islands on the flexible carrier. This means silicon segments may be incorporated below selected parts of the interposer. This provides additional support during manipulation and/or assembly of the transducer and the wires to the interposer. An additional benefit is that the electrical contacts can all be made on the same side of the interposer, thereby ensuring a better uniformity of the electrode surfaces.

FIG. 7 shows a first variant example in which the interposer has silicon support segments 80, 82, functioning as base units, below both the transducer area and the wire connection area. This provides optimal support during assembly of the transducer interposer and connection of the wires.

Figures 7A, 7B, 7C, 7D, 7E:
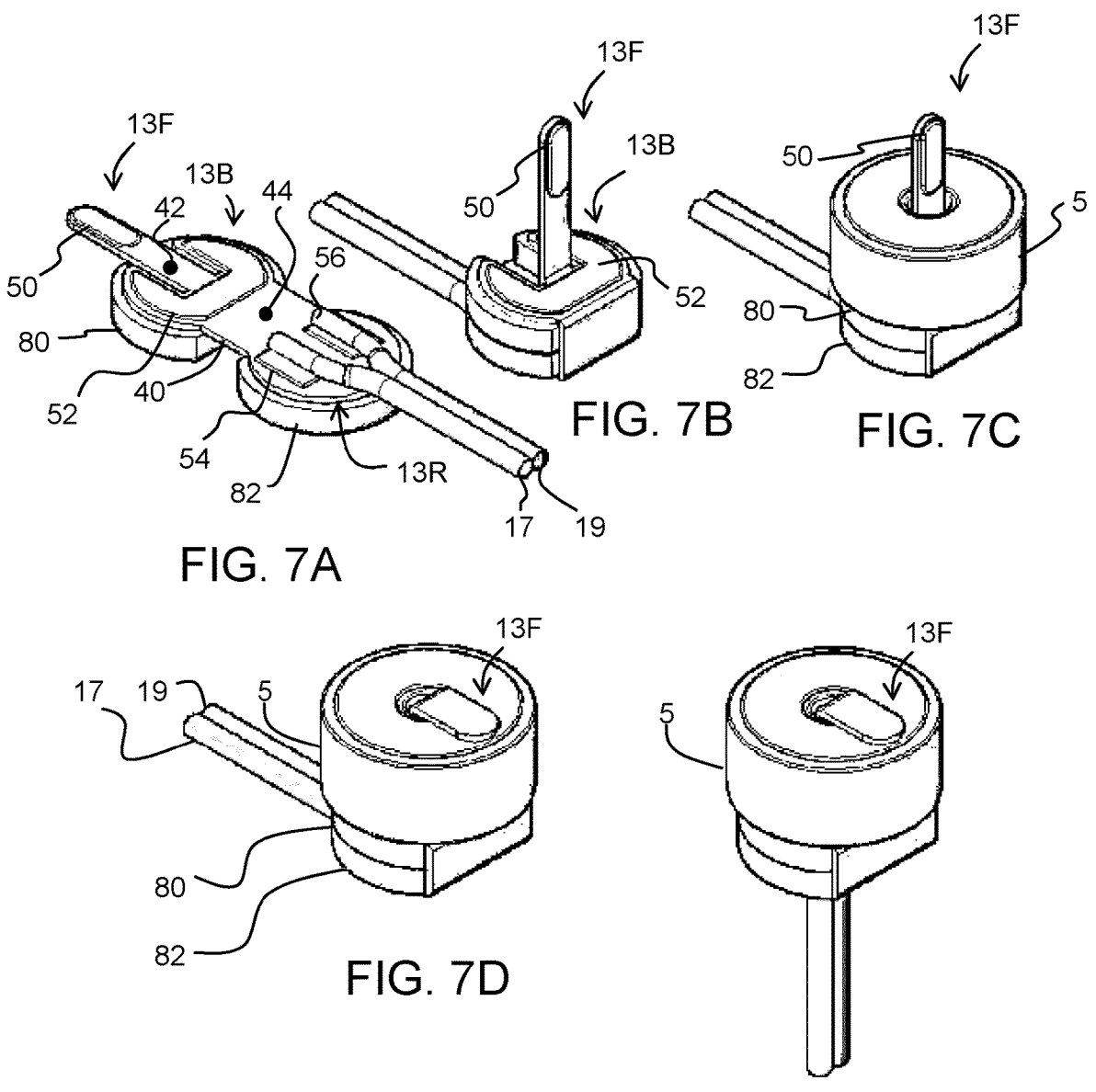
FIGS. 7A to 7E show a fourth example of a sensor in accordance with the invention.

FIG. 7A shows the interposer as manufactured. The external wire connections are made in this initial configuration.

This example is based on a sensor element with a central opening. The first and second terminal segments 13F, 13B and the intermediate segment are the same as in the design of FIG. 5, with the first and second contact terminals 50, 52 on the same side.

The third and fourth contact terminals 54, 56 are on a third, more remote, terminal segment 13R of the interconnect. The third terminal segment 13R is interconnected to the second terminal segment 13B by a second intermediate segment 44.

The third and fourth contact terminals 54, 56 are on the same side of the interposer as the first and second contact terminals 50, 52. Thus, all four contact terminals are now on the same side of the interposer.

The first and second contact terminals 50, 52 wrap around the sensor element in the same way as explained above. The third and fourth contact terminals may then be positioned in a variety of positions by bending the second intermediate segment 44.

FIG. 7B shows the interposer after the intermediate segment is bent to 90 degrees, so that the first contact terminal can be pushed through a central opening of a sensor element. The silicon support segments 80,82 are folded over on top of each other, and the third terminal segment 13R is parallel and beneath the second terminal segment 13B.

FIG. 7C shows the sensor element 5 mounted over the projecting first contact terminal 50.

FIG. 7D shows the interposer after the first contact terminal has been bent around so that the first contact terminal 50 is positioned against the first side 11 (front) of the sensor element and the first contact terminal 50 makes electrical contact with a terminal of the sensor element 5.

FIG. 7E shows the wires bent down to be parallel to the elongate axis, e.g. of the catheter.

The silicon segment 82 below the external wire connection area has an additional benefit: it facilitates the wire connection process as wire bonding on silicon is well-known and a better controllable process than bonding directly on a flex that is glued to the transducer backside surface.

The silicon segment 82 below the wire connection area also allows multiple orientations of the wire ends relative to the transducer. For example, the wire connection area can be parallel to the transducer electrode planes. This requires 90 degree bending of the wires, for example as seen in FIGS. 4 and 5.

FIG. 8 shows an example which avoids these wire bends.

Figures 8A, 8B:
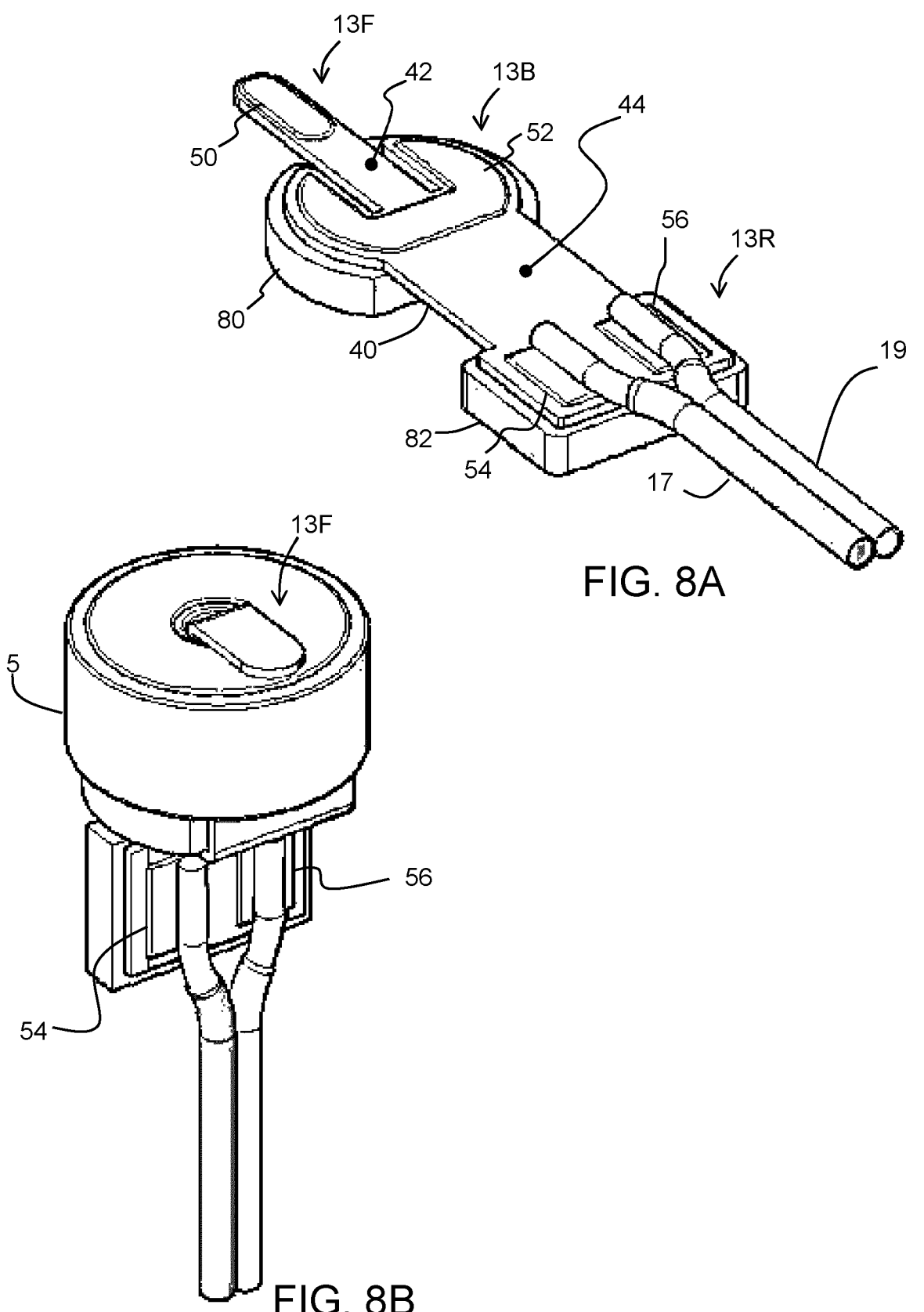
FIGS. 8A to 8B show a fifth example of a sensor in accordance with the invention.

FIG. 8A corresponds to FIG. 7A. FIG. 8B shows the wire connection area perpendicular to the transducer electrode planes. This prevents the need for bending the wire ends. The disadvantage is that this arrangement might add to the stiff length of the transducer tip, which has an adverse effect on the guidewire tip flexibility.

FIGS. 7 and 8 shows a parallel orientation of the two wire connection pads.

Figures 9A, 9B, 9C, 9D, 9E:
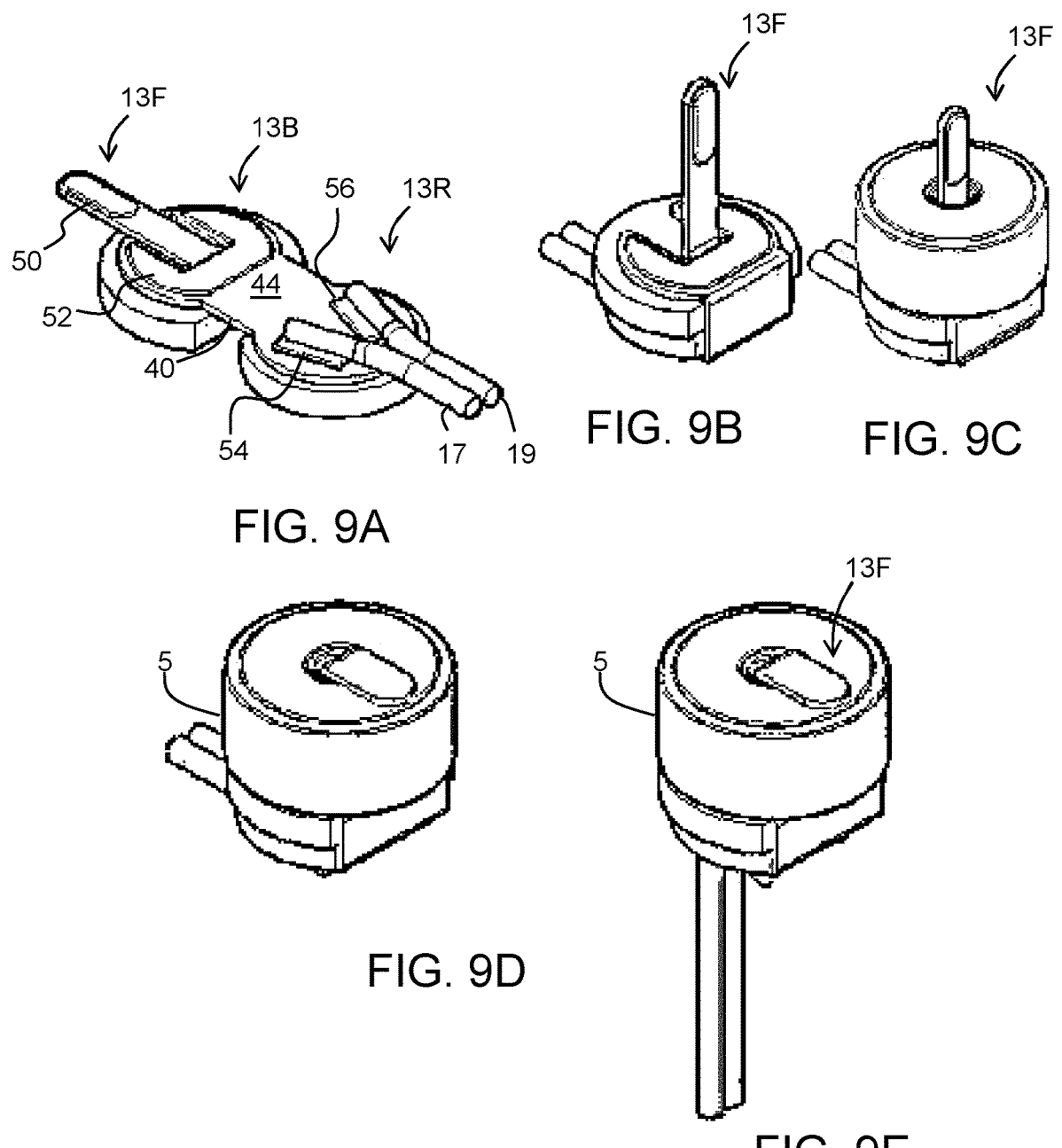
FIGS. 9A to 9E show a sixth example of a sensor in accordance with the invention.
Figure 10A:
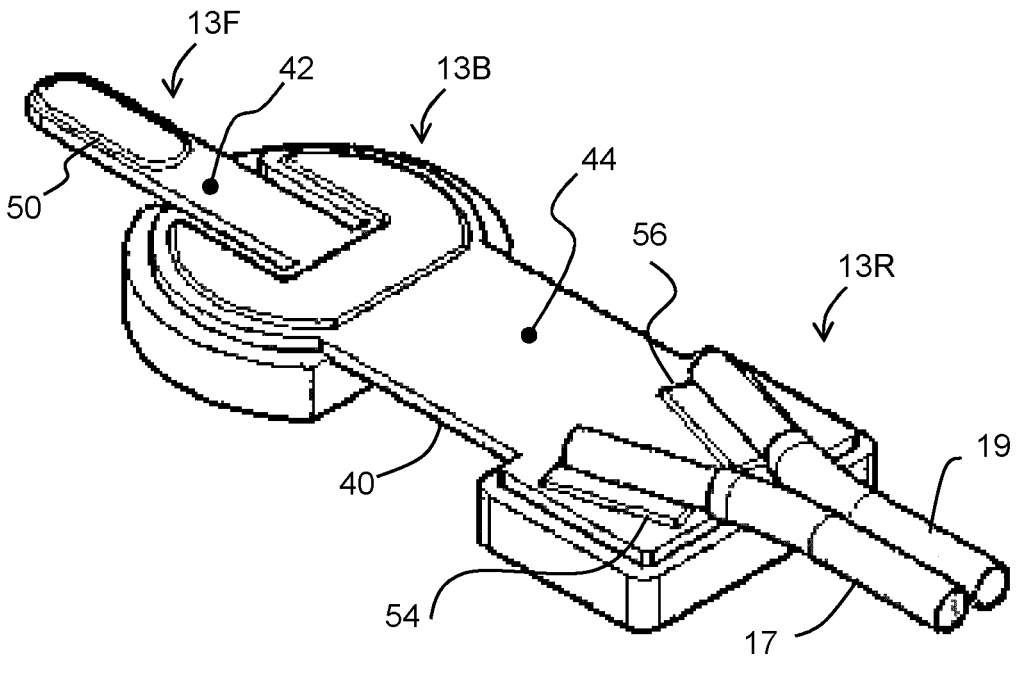
FIGS. 10A to 10B show a seventh example of a sensor in accordance with the invention.
Figure 10B:
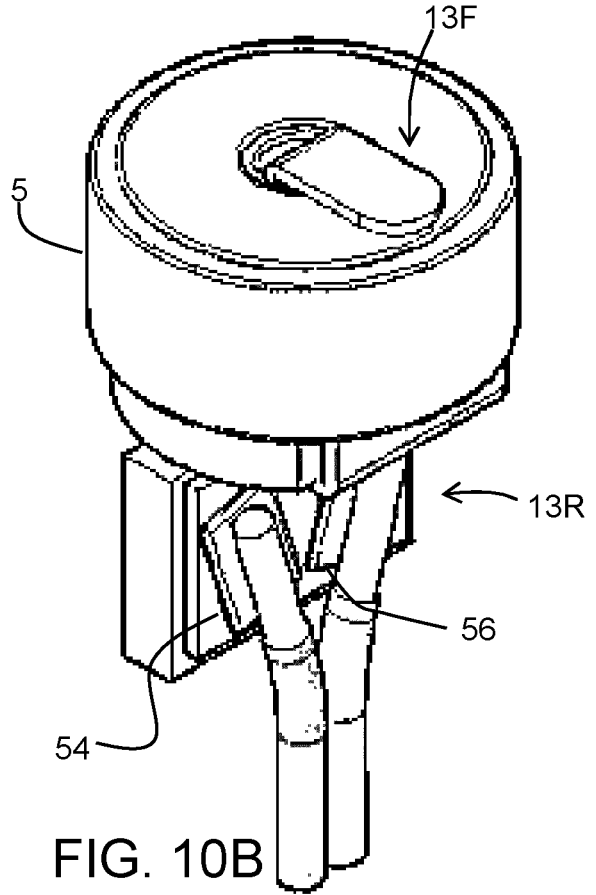

FIGS. 9 and 10 show a modification to FIGS. 7 and 8 with a V-shaped orientation for the third and fourth connection terminals 54,56.

FIGS. 9A to 9E show the stages of implementation corresponding to FIGS. 7A to 7E, and FIGS. 10A and 10B correspond to FIGS. 8A and 8B.

This V-shaped orientation is expected to ease wire connection, as it prevents the need for a double S-shape bend of the wire ends. On the other hand, in some cases this may increase the required width of the wire connection segment somewhat, so this may not be feasible in certain tight housing configurations.

FIG. 11 shows a modification to FIG. 10 in which there is only a support segment 82 below the third terminal segment 13R i.e. below the third and fourth contact terminals.

Figures 11A, 11B:
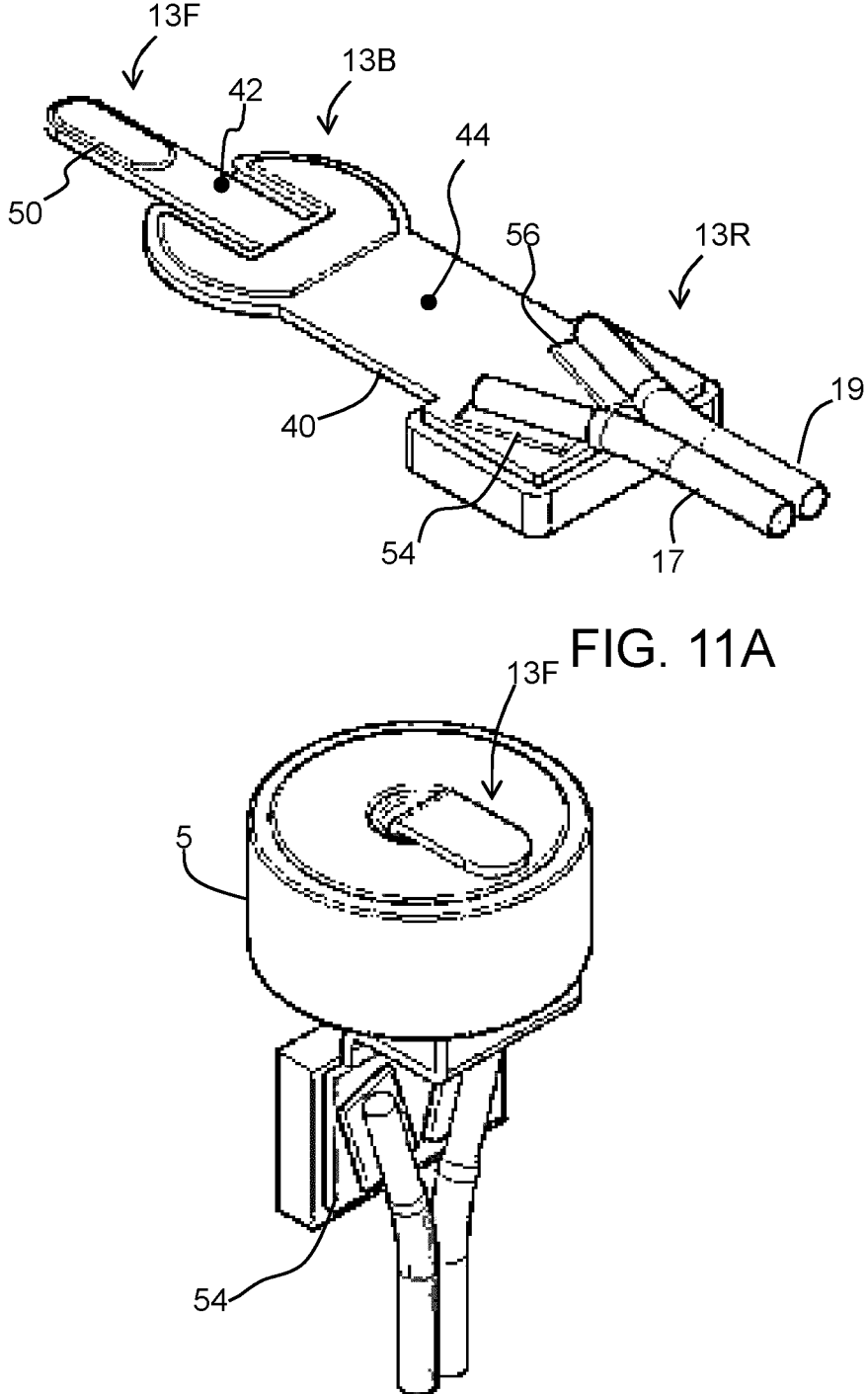
FIGS. 11A to 11B show an eighth example of a sensor in accordance with the invention.

FIG. 11A shows the manufactured configuration and FIG. 11B shows the configuration in use.

A potential disadvantage of the use of a silicon segment at the interposer area directly below the transducer, is that it may adversely affect the vibration behavior of the transducer. Therefore, FIG. 11 is without such a silicon segment directly below the transducer. This example has the wire connection area oriented perpendicular to the transducer electrode planes, and has a V-shaped orientation of the two wire connection pads, but it can be understood that removal of the silicon segment directly below the transducer can be combined with any of the other interposer variations.

As an alternative to simply omitting the silicon segment from the interposer area directly below the transducer, one or more suitable acoustic de-matching or attenuating backing layers may be added, e.g. by means of adhesive bonding to the interposer bottom side.

FIG. 12 shows an example.

FIG. 12A shows an insert 120, The insert may be a de-matching layer such as a dense, high modulus metal, such as molybdenum or tungsten, or a high density ceramic, such as tungsten carbide. The insert may be an attenuating backing layer such as an epoxy with aluminum oxide or glass filler. This alternative of including suitable de-matching or attenuating backing layers at the interposer bottom side can be combined with any of the other interposer variations.

FIGS. 12B to 12F correspond to FIGS. 9A to 9E, respectively, with the insert taking the place of the silicon segment 80.

An alternative to connecting the wire ends while they are parallel to the wire connection pads, is to insert them in suitable openings created in the wire connection area.

FIG. 13 shows this alternative wire connection approach applied to the general design of FIG. 9.

Figures 13A, 13B, 13C, 13D, 13E:
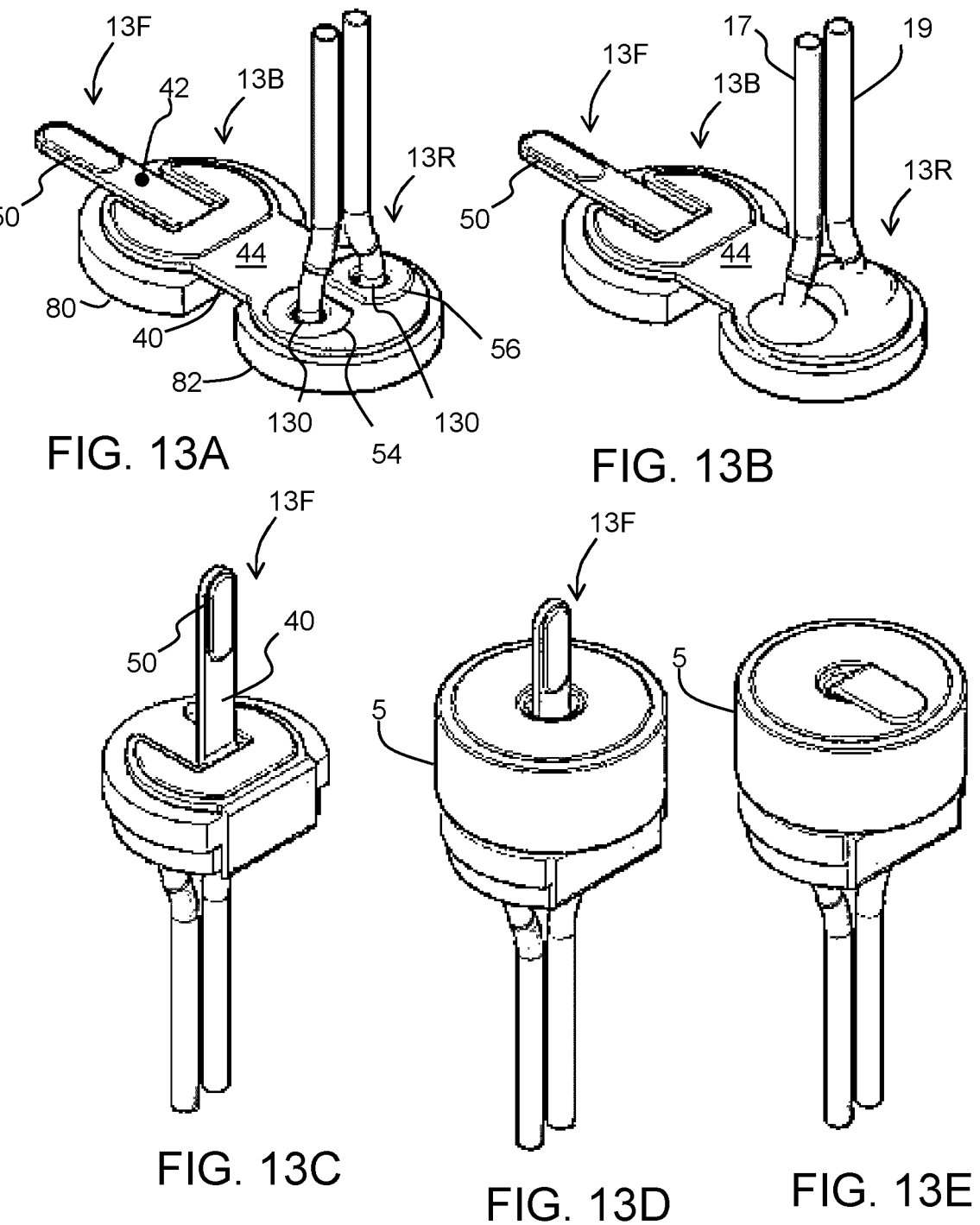
FIGS. 13A to 13E show a tenth example of a sensor in accordance with the invention.

FIG. 13A shows the interposer as manufactured. The external wire connections are made in this initial configuration. Openings 130 are formed in the third terminal segment 13R. Around these openings, metal pads have been created that may be used to solder the wires in place. Advantages are a relatively short rigid tip length and this prevents the need for bending the wire ends.

FIG. 13A shows the configuration before wire soldering, and FIG. 13B shows the configuration after wire soldering.

FIG. 13C shows the first contact terminal 50 bent up and the third terminal segment 13R folded around the two silicon segments 80,82.

FIG. 13D shows the introduction of the sensor element 5 and FIG. 13E shows the final stage of bending the first contact terminal over the sensor element.

In all of the above embodiments, the wire connection is relatively close to the transducer. This assumes (quasi) rigid potting of the transducer subassembly including wire connections in some sort of housing using a suitable potting material. In this approach, a short stiff tip length is sought after, as this is preferred for highest guidewire tip flexibility.

Alternatively, the length of the flexible part of the interposer may be increased, e.g. to 3 cm, such that the wire connection no longer forms part of the rigid tip, thus reducing the rigid tip length in another way.

An example embodiment having a long flexible part forming the second intermediate segment 44 is shown in FIG. 14.

Figures 14A, 14B:
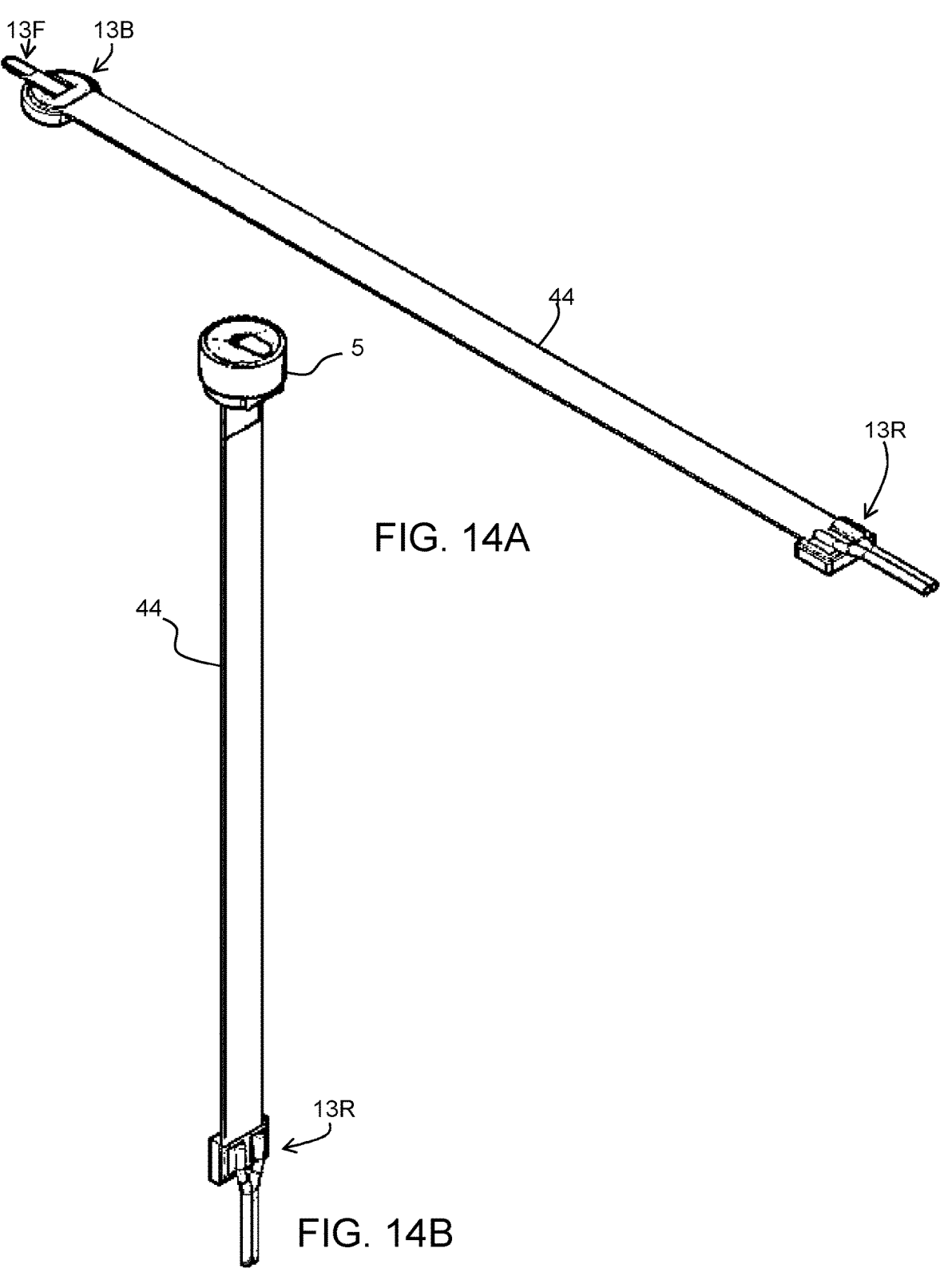
FIGS. 14A to 14B show an eleventh example of a sensor in accordance with the invention.

FIG. 14A shows the interposer and FIG. 14B shows the connected sensor element as well. This is shown as a modification to the example of FIG. 7.

Using such an approach, the guidewire tip flexibility may be increased beyond what is feasible using any of the other known methods. This approach of leading the wire connections away from the transducer region may also solve space constraint issues that may be present at the transducer region, or possibly proximal to the transducer region, e.g. when multiple sensors are integrated in the same guidewire, e.g. for flow as well as pressure sensing.

FIG. 15 shows two further examples.

Figures 15A, 15B:
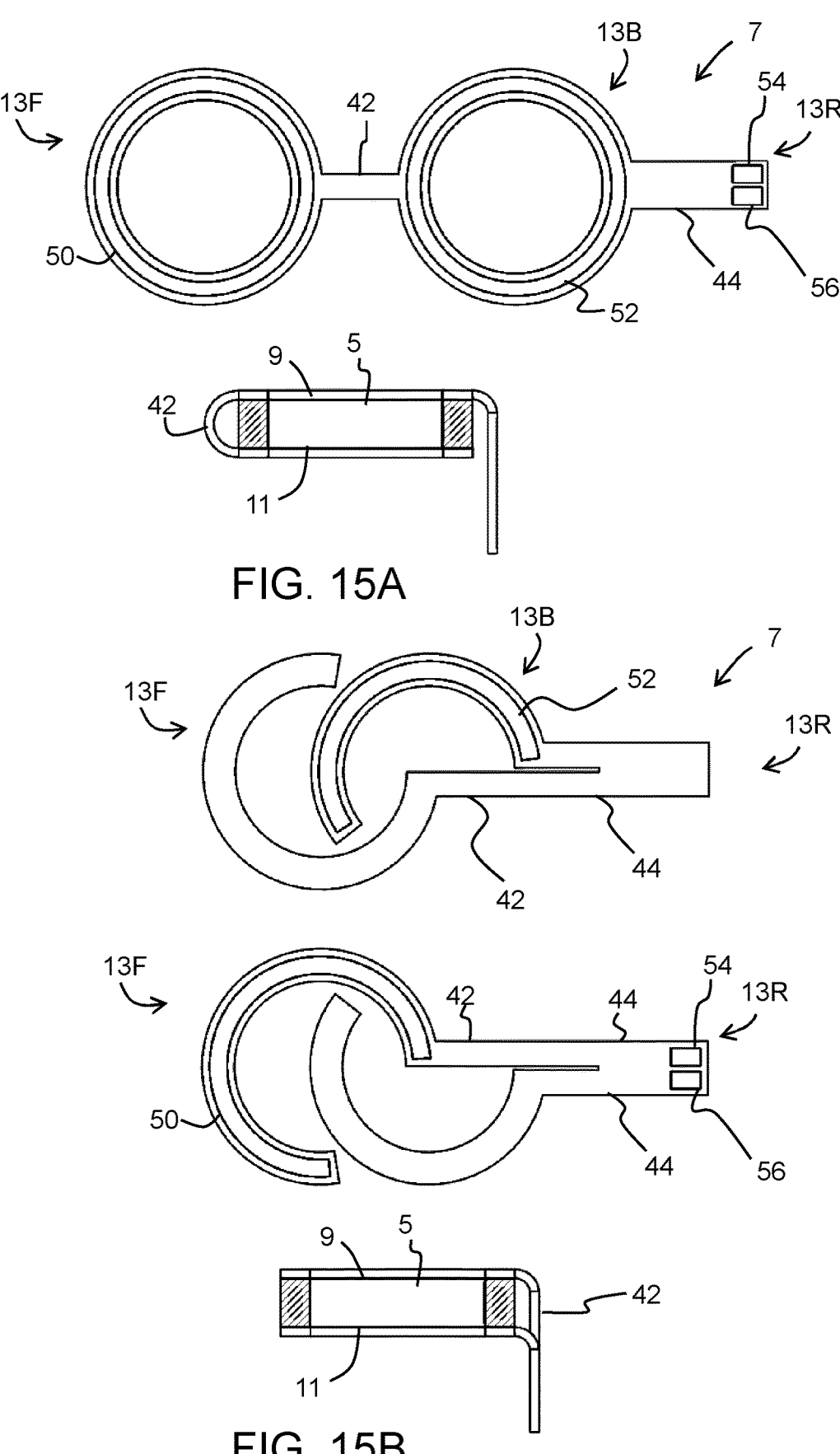
FIGS. 15A to 15B show a twelfth example of a sensor in accordance with the invention.

FIG. 15A shows an example of a sensor with the interconnect in unfolded plan view in the top image, and in side view coupled to a sensor element 5 in the bottom image. FIG. 15B shows an example of a sensor with the interconnect in unfolded in plan view of one face (e.g. a top view) in the top image, in plan view of an opposite face (e.g. a bottom view) in the middle image, and in side view coupled to a sensor element 5 in the bottom image.

In both cases, and as in the examples above, the interconnect 7 comprises an electrically insulating flexible carrier with first and second terminal segments 13B,13F interconnected by an intermediate segment 42.

The first terminal segment 13F comprises a first contact terminal 50 on a surface facing the first side 11 and the second terminal segment 13B comprises a second contact terminal 52 on a surface facing the second side 9. The interconnect further comprises third and fourth, external, contact terminals 54, 56 and the internal electrical connections described above.

The third and fourth contact terminals 54, 56 are on a third terminal segment 13R which is interconnected to the second terminal segment 13B by a second intermediate segment 44.

In FIG. 15A, the contact terminals are all on the same surface, and the intermediate segment folds around the sensor.

In FIG. 15B, the first and second contact terminals are on opposite faces of the interconnect. One is folded under the sensor and the other is folded over the sensor. This means all bridging parts are to one side of the sensor.

These are just further examples of possible configurations.

It is noted that all interposer variants having at least one of the silicon segments 80, 82 (which may be realized by means of the Flex-to-Rigid technology) may contain electronic ASIC functionality. The function of this electronics can be signal amplification, multiplexing signals from multiple sensors, or any other relevant electronic function or combination of functions.

Even though the emphasis has been on guidewires, the invention is also applicable to other catheter-like devices, such as a micro catheter, having similar flow sensing or position tracking functionality. The main difference between a guidewire and a micro catheter is that a micro catheter is a hollow tube, suitable to contain a guidewire in its main lumen. Therefore, the outer diameter of a micro catheter is larger, and when a circular disk including a central hole is used for the piezo transducer, the hole of the transducer is larger in order to fit the guidewire.

Figure 16A:
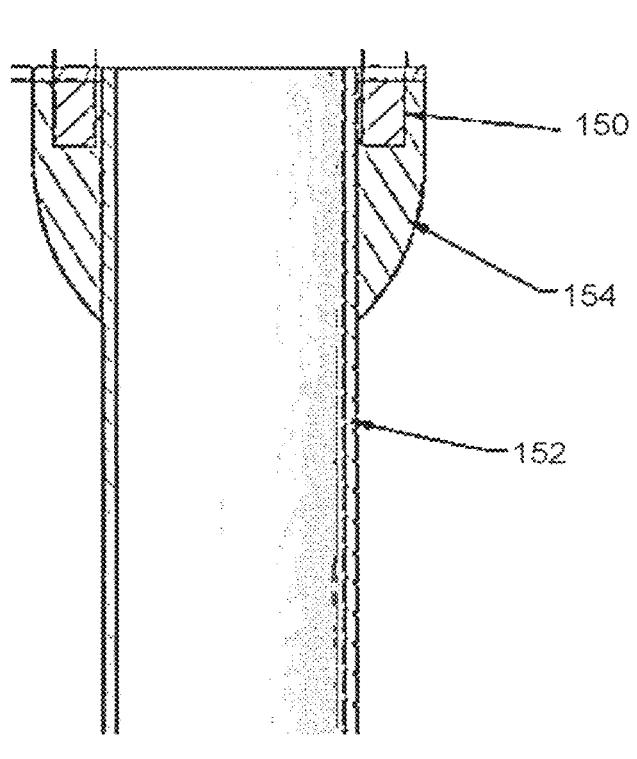
FIGS. 16A and 16B show a catheter, in cross section and in perspective cut away view respectively.
Figure 16B:
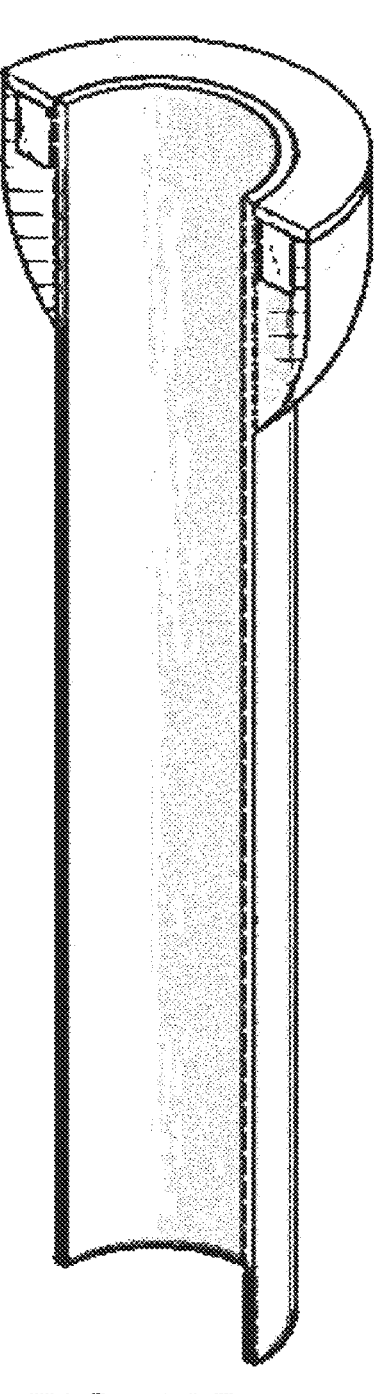

FIG. 16 shows a catheter, in cross section in FIG. 16A and in perspective cut away view in FIG. 16B. The transducer 150 has an annular shape around the inner tube 152 of the catheter. The transducer is held by glue layer 154 with backing and/or dematching characteristics. The transducer may for example comprise piezo transducer for blood flow measurements.

In all examples above, the sensor may be used for several medical applications such as for Doppler flow measurement, ultrasound imaging. Furthermore, ultrasound tracking of the sensor by an external ultrasound probe is also enabled.

The sensor may comprise an acoustic stack of materials, including active and passive parts. A sensor element is the active part, which generates/receives ultrasound waves. The sensor element can comprise a ceramic disk or a plate of any geometrical form (circular, square, hexagonal, octagonal, etc.). The passive parts of the sensor play a role in coupling acoustic waves effectively into the desired medium.

The passive parts are provided by one or more matching layers in front of the active part, and one or more de-matching layers at the back of the active part. The de-matching layers can comprise backing material for attenuating transmission of ultrasound waves in undesired directions (e.g. proximal shaft of the device). The de-matching layers can comprise non-conducting epoxy material. The active parts can comprise single crystal piezo electric material. The matching layers for efficiently coupling ultrasound waves into a medium in the desired direction (e.g. anatomical structures, various body fluid, etc.).

The sensor element(s) may comprise a piezoelectric ultrasound emitter/sensor array or a capacitive micro-machined ultrasound emitter/sensor array. The sensor element(s) may comprise multiple or single acoustic stack of materials. Ultrasound emitter/receiver elements or transducer elements provide an increased aperture for receiving ultrasound scattering and reflection from anatomical media (structures, fluids) upon impinging ultrasound waves.

The contact terminals of the interposer for example comprises metal, e.g. gold (Au) or other noble metals like platinum (Pt). Au or other noble metals like Pt may be preferred for preventing corrosion. If properly shielded, silver (Ag) can also be used. The thickness of the metallic layer is in the range of about 10 to 500 nanometer preferably about 30 to 50 nanometer (including tolerances).

The need for additional soldering material on the transducer surface, as in the prior art, is avoided when replacing the soldered wire with the interconnect described herein. Also, the interconnect provides less detrimental acoustic influence or even enhance acoustic pressure output.

The wires 17, 19 are for example provided with a metallic layer comprising Au, Pt, Ag or other noble metals, at least in the region where the wires 17, 19 are to contact the contact terminals.

A sensor element used with an interconnect as described herein may comprise a matching layer thickness of 20 to 100 micron. At a predetermined frequency, for example between 6-45 MHz, the thickness of the carrier can be part of the matching layer, or form entirely on its own the matching layer. The thickness of the first terminal segment 13F in any of the embodiments is preferably chosen such that it acts as a quarter-wavelength ($\lambda$/4) acoustic matching layer, bridging the large acoustic impedance mismatch between the piezoelectric material and the anatomy of the human body.

While the invention has been illustrated, and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims. In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A sensor, comprising:
a sensor element with first side and second side opposite the first side; and
an interconnect comprising a flexible carrier that is electrically insulating, wherein the interconnect comprises first and second terminal segments interconnected by an intermediate segment,
wherein the first terminal segment is positioned against the first side of the sensor element and comprises a first contact terminal on a surface facing the first side,
wherein the second terminal segment is positioned against the second side of the sensor element and comprises a second contact terminal on a surface facing the second side,
wherein the interconnect further comprises third and fourth external contact terminals, and
wherein the interconnect further comprises a first internal electrical connection within the flexible carrier which connects the first contact terminal and the fourth contact terminal and a second internal electrical connection within the flexible carrier which connects the second contact terminal and the third external contact terminal.

2. The sensor of claim 1, wherein the third and fourth external contact terminals are on the second terminal segment, on the opposite side of the flexible carrier to the second contact terminal.

3. The sensor of claim 1, wherein the third and fourth external contact terminals are on a third terminal segment of the interconnect, the third terminal segment being interconnected to the second terminal segment by a second intermediate segment.

4. The sensor of claim 3, wherein the third and fourth external contact terminals are on the same side of the flexible carrier as the second contact terminal.

5. The sensor of claim 3, wherein:
the second terminal segment is connected to a first base unit; and/or the third terminal segment is connected to a second base unit.

6. The sensor of claim 5, wherein:
the first base unit is a de-matching or attenuating backing layer for the sensor element; and/or
the first or second base unit comprises active electronic components.

7. The sensor of claim 5, wherein the second intermediate segment extends around an outer edge of the first and/or second base unit.

8. The sensor of claim 7 comprising first and second base units, wherein the second intermediate segment extends around an outer edge of the first base unit and the second base unit extends at 90 degrees to the first base unit.

9. The sensor of claim 1, further comprising a first wire connected to the third external contact terminal and a second wire connected to the fourth external contact terminal.

10. The sensor of claim 9, wherein the first and second wires each have ends which are connected to the third and fourth external contact terminals:
parallel to a plane in which the third and fourth external contact terminals extend; or
perpendicular to the plane in which the third and fourth external contact terminals extend.

11. The sensor of claim 1, wherein the intermediate segment of the flexible carrier is located adjacent to a lateral outer side of the sensor element and the first and second terminal segments are folded over the first side and the second side of the sensor element.

12. The sensor of claim 1, wherein the sensor element comprises a central opening, the intermediate segment is bent relative to the second terminal segment, the intermediate segment of the flexible carrier passes through the central opening, and the first terminal segment is folded over the first side of the sensor element.

13. The sensor of claim 1, wherein the sensor element is an ultrasound sensor element.

14. An interventional medical device, comprising:
a sensor according to claim 1; and
an elongate body,
wherein the sensor is mounted at a distal end of the elongate body.

15. A method of manufacturing a sensor, comprising:
providing a sensor element with two opposite sides;
providing an interconnect comprising a flexible carrier that is electrically insulating, wherein the flexible carrier comprises first and second terminal segments interconnected by an intermediate segment;
bending the interconnect such that:
the first terminal segment is against a first side of the two opposite sides of the sensor element with a first contact terminal facing the first side; and
the second terminal segment is against a second side of the two opposite sides of the sensor element with a second contact terminal facing the second side; and
using the interconnect to provide a first internal electrical connection within the flexible carrier which connects the first contact terminal to a fourth external contact terminal and to provide a second internal electrical connection within the flexible carrier which connects the second contact terminal to a third external contact terminal.

\* \* \* \* \*